(12) United States Patent
Strauss

(10) Patent No.: US 7,425,326 B2
(45) Date of Patent: Sep. 16, 2008

(54) USE OF COLLAGENASE TO FACILITATE GUIDE WIRE CROSSING IN TOTAL ARTERIAL OCCLUSIONS

(76) Inventor: Bradley H. Strauss, 50 Viewmount Avenue, Toronto, ON (CA) M6B 1T4

( * ) Notice: Subject to any disclaimer, the term of this patent is extended or adjusted under 35 U.S.C. 154(b) by 0 days.

(21) Appl. No.: 11/534,351

(22) Filed: Sep. 22, 2006

(65) Prior Publication Data

US 2007/0014783 A1    Jan. 18, 2007

Related U.S. Application Data

(63) Continuation of application No. 10/491,424, filed as application No. PCT/CA02/01476 on Oct. 1, 2002, now abandoned.

(60) Provisional application No. 60/325,539, filed on Oct. 1, 2001.

(51) Int. Cl.
*A61K 38/48* (2006.01)
*C12N 9/50* (2006.01)
*A61B 17/3207* (2006.01)

(52) U.S. Cl. .................. 424/94.67; 435/219; 606/7
(58) Field of Classification Search .............. 424/94.67; 435/219; 606/7
See application file for complete search history.

(56) References Cited

U.S. PATENT DOCUMENTS

| | | | |
|---|---|---|---|
| 4,636,195 A | 1/1987 | Wolinsky | |
| 5,024,829 A | 6/1991 | Berger et al. | |
| 5,163,421 A | 11/1992 | Bernstein et al. | |
| 5,328,470 A | 7/1994 | Nabel et al. | |
| 5,422,261 A | 6/1995 | Lee et al. | |
| 5,503,850 A | 4/1996 | O'Rear, III et al. | |
| 5,813,949 A | 3/1997 | Miraki | |
| 5,955,584 A | 9/1999 | Ditlow et al. | |
| 6,306,166 B1 | 10/2001 | Barry et al. | |
| 2002/0077594 A1 | 6/2002 | Chien et al. | |
| 2002/0082221 A1 | 6/2002 | Herrmann et al. | |

FOREIGN PATENT DOCUMENTS

| | | |
|---|---|---|
| EP | 0 920 882 A2 | 6/1999 |
| EP | 1060747 A | 12/2000 |
| WO | 03/028639 A | 4/2003 |

OTHER PUBLICATIONS

Yoon, H.C. et al., "A Porcine Model of Chronic Peripheral Arterial Occlusion," Journal of Vascular and Interventional Radiology: JVIR. United States, 1996, Jan.-Feb., vol. 7, No. 1, Jan. 1996, pp. 65-74 (XP009003811) (ISSN: 1051-0443) "Surgical and Angiographic Protocol" (10 pages).

(Continued)

*Primary Examiner*—Jon P Weber
*Assistant Examiner*—Rosanne Kosson
(74) *Attorney, Agent, or Firm*—Torys LLP

(57) ABSTRACT

The use of a collagenase containing formulation for degrading collagen within an occlusive atherosclerotic plaque in a chronic fibrotic occlusion, chronically occluded animal tube or cavity. A medical-related apparatus is provided comprising a medical-related device having provided thereto a therapeutic amount of a collagen degrading composition comprising a proteiolytic enzyme containing formulation. A method is provided for treating chronically occluded animal tubes and cavities by administering a therapeutic effective amount of a proteolytic enzyme-containing formulation adjacent to an occluding atherosclerotic plaque, waiting for a pre-angioplasty waiting period, followed by crossing the plaque with an angioplasty guide wire.

95 Claims, 10 Drawing Sheets

OTHER PUBLICATIONS

Kerenyi et al., "Local enzymatic treatment of atherosclerotic plaques," Exp Mol Path 49:330-338, 1988 (9 pages).

Sigma-Aldrich catalog excerpt for collagenase Type 1A from Colstridium histolyticum, http://www.sigmaaldrich.com/catalog/search/Search Results Page/Expand, printed on Jan. 12, 2006 (3 pages).

International Union of Biochemistry and Molecular Biology, Enzyme Nomenclature on line, EC 3.4.24.3, record for collagenase, http://www.chem.qmul.ac.uk/iubmb/enzyme/EC3/4/24/3.html, printed on Jan. 12, 2006 (2 pages).

Sionis et al., "Chronic Total Coronary Occlusions: A Review of their Special Features and the Existing Techniques of Percutaneous Treatment," Hellenic Journal of Cardiology, 44:136-142, 2003 (7 pages).

Puma et al., "Percutaneous revascularization of chronic coronary occlusions: an overview," J Am Coll Cardiol 26(1):1-11, 1995 (11 pages).

Enzyme Nomenclature (Web Version of Enzyme Nomenclature Committee of the International Union of Biochemistry and Molecular Biology (NC-IUBMB), record for t-PA and urokinase at http://www.chem.qmul.ac.uk/iubm/enzyme/EC3/4/21/88.html, printed on May 15, 2006 (2 pages).

Enzyme Nomenclature (Web Version of Enzyme Nomenclature Committee of the International Union of Biochemistry and Molecular Biology (NC-IUBMB), record for urokinase at http://www.chem.qmul.ac.uk/iubm/enzyme/EC3/4/21/73.html, respectively, printed on May 15, 2006 (1 pages).

International Search Report from PCT Application No. PCT/CA2005/000539 filed Apr. 8, 2005 (3 pages).

Stone, Gregg W., et al, Parcutaneous Recanalization of Chronically Occluded Arteries. A Consensus Document, Circulation, Oct. 11, 2005, 2364-72, vol. 112, 2005 American Heart Association, Inc. (9 pages).

Strauss, Bradley H., et al, Collagenase Plaque Digestion for Facilitating Guide Wire Crossing in Chronic Total Occlusions, Circulation, Sep. 9, 2003, 1259-1262, vol. 108(10), 2003 American Heart Association, Inc. (4 pages).

Zidar, Frank J. et al, Prospective, Randomized Trial of Prolonged Intracoronary Urokinase Infusion for Chronic Total Occlusions in Native Coronary Arteries, JACC, May 1998, 1408-12, vol. 27, No. 8, American College of Cardiology (7 pages).

Hartmann, Joseph R., et al, Recanalization of Chronically Occluded Aortocoronary Saphenous Vein Bypass Grafts by Extended Infusion of Urokinase, Initial Results And Short-Term Clinical Follow-Up, JACC, Nov. 15, 1991, 1517-23, vol. 18, No. 9, American College of cardiology (7 pages).

Ruocco, Jr., Nicholas A., et al, Experience with Low-Dose Intracoronary Recombinant Tissue-Type Plasminogen Activator for Nonacute Total Occlusions Before Percutaneous Transluminal Coronary Angioplasty, The American Journal of Cardiology, Dec. 15, 1991, 1609-13, vol. 68 (5 pages).

Hartmann, Joseph, et al, Prolonged Infusion of Urokinase for Recanalization of Chronically Occluded Aortocoronary Bypass Grafts, The American Journal of Cardiology, Jan. 1, 1988, 189-191, vol. 61 (3 pages).

Braunwald, Eugene, et al, (Editors), Braunwald's Heart Disease, A Textbook of Cardiovascular Disease, 5th Edition, 1997, Chapter 58, pp. 1814-1815, W.B. Saunders Co. (2 pages).

Topol, Eric J., et al., (Editors), Textbook of Interventional Cardiology, 3rd Edition, 1999, Chapter 5, pp. 78-79, W.B. Saunders Co. (2 pages).

European Search Report and Annex thereto, established on European Patent Office Application No. 2,764,443, (3 pages) Apr. 24, 2007.

Claims 1-22 on which Search Report on European Patent Office Application No. 2,764,443 of Apr. 24, 2007 was established.

Kumar, Vinay et al., Tissue Renewal and Repair; Regeneration, Healing, and Fibrosis, Chapter 3, In: Robbins & Coltran Pathologic Basis of DIsease, Seventh Edition, Philadelphia 2005: pp. 107, 110, 111, 115 and 116.

Song, Woohyuk et al., Rapid Communication: A New Percutaneous Porcine Coronary Model of Chronic Total Occlusion, The Jounal of Invasive Cardiology. Sep. 9, 2005 17(9): pp. 452-454.

Yoon, Hyo-Chun, et al., A Porcine Model of Chronic Peripheral Arterial Occlusion, Journal of Vascular and Interventional Radiology, Jan. 1996; 7: pp. 65-74.

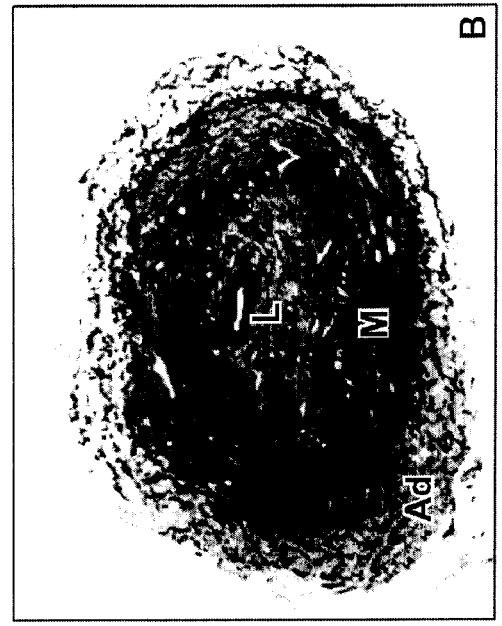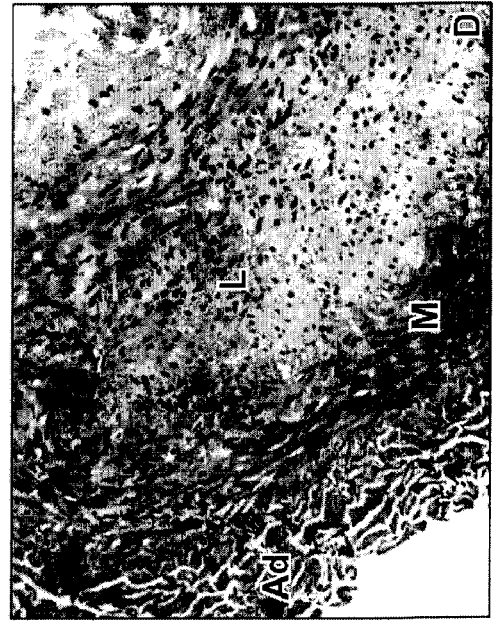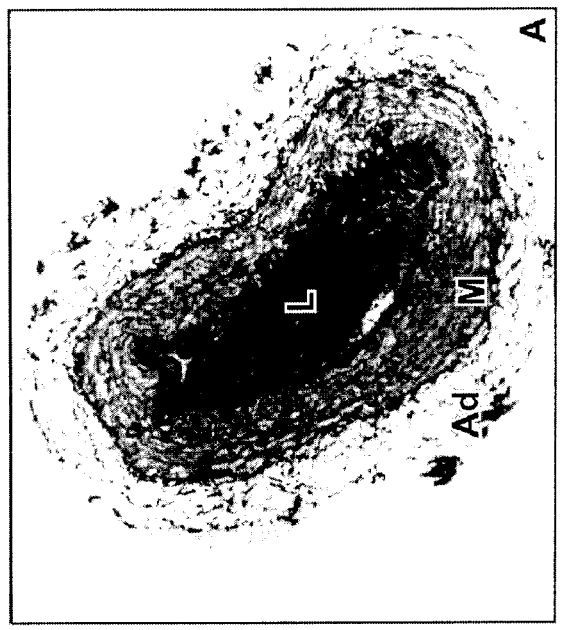
Figure 1

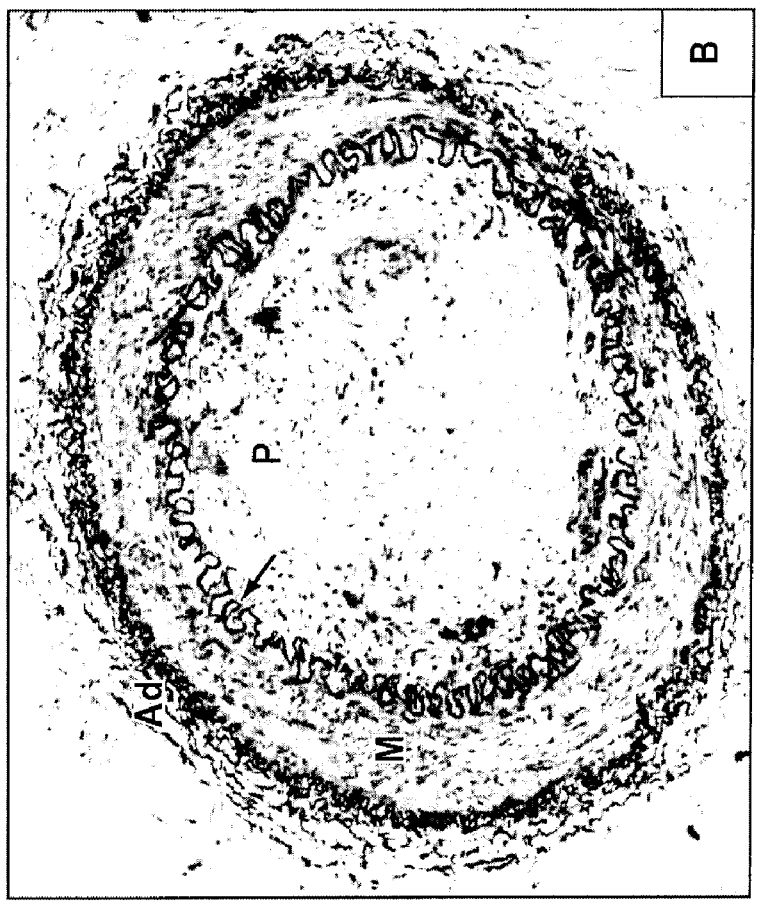
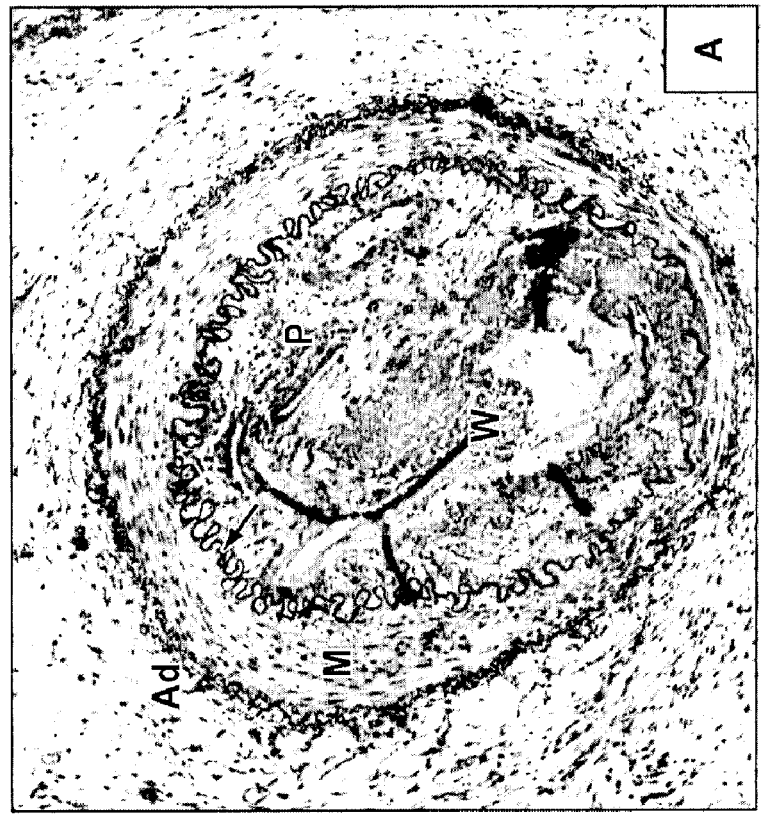
Figure 4

Figure 6: Guide Wire Crossings at 72 Hr Randomized, Blinded n=27

Figure 7: Western Blotting Using Antibody Against Interstitial Collagenase

Lanes 1 and 2– Collagenase treated arteries, 24 hours
Lanes 3 and 4– Placebo treated arteries, 24 hours
Lanes 5– Collagenase (20 μg)

Figure 8: Gelatin Zymogram

Lane 1 - Collagenase treated artery, 24 hours
Lane 2 - Placebo treated artery, 24 hours Figure 9: Western Blotting Using Antibody Against Degraded Collagen Lanes 1 and 2 - Collagenase treated arteries, 24 hours Lanes 3 and 4 - Placebo treated arteries, 24 hours

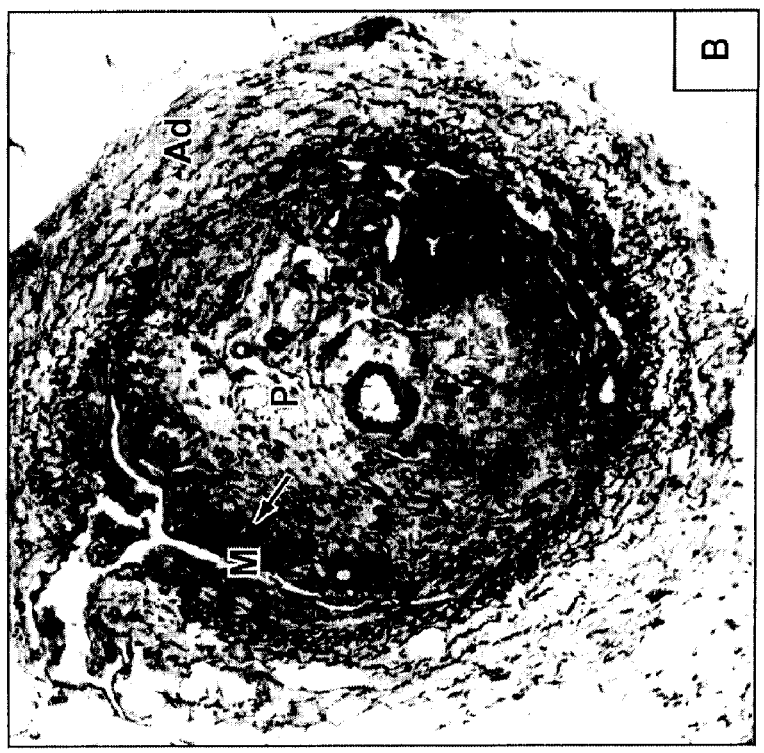
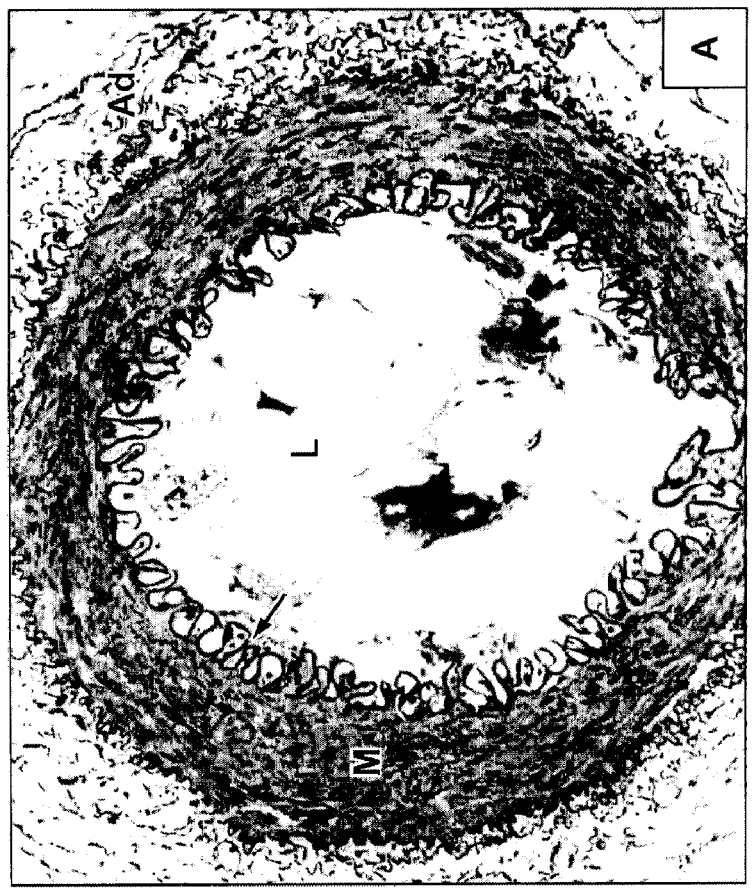
Figure 10

USE OF COLLAGENASE TO FACILITATE GUIDE WIRE CROSSING IN TOTAL ARTERIAL OCCLUSIONS

RELATED APPLICATIONS

This application is a continuation application of U.S. patent application Ser. No. 10/491,424, filed Apr. 1, 2004 and completed Oct. 4, 2004, which application is a national stage entry (371) application of international patent application No. PCT/CA02/01476 filed Oct. 1, 2002, now expired, and claims priority from U.S. Provisional Patent Application Ser. No. 60/325,539, filed Oct. 1, 2001.

FIELD OF THE INVENTION

The present invention relates to the field of percutaneous interventions of occluded arteries using local infusion of collagenase or a combination of enzymes that include collagenase.

BACKGROUND OF THE INVENTION

Scope of Problem:

Chronic total occlusions (CTO) are an extremely common finding in patients undergoing diagnostic catheterization. Up to 20% of patients undergoing angiography have been reported to have one or more chronic total coronary occlusions[1]. Balloon angioplasty is one treatment modality for CTO with the first successful report appearing in 1982[2]. Percutaneous coronary interventions (PCI) continue to increase annually with >1 million procedures world-wide in 1998[3], and CTO currently account for approximately 10%-15% of PCI[4-7]. However, since PCI have severe limitations in this patient subset, clinicians frequently decide to refer these patients for bypass surgery or persist with (often ineffective) medical therapy. The presence of one or more CTO of vessels supplying viable areas of myocardium remains one of the most common reasons for referral for bypass surgery rather than attempting PCI.

Limitations of PCI

The main limitations of PCI for CTO are the decreased procedural success rates compared to stenotic (but not totally occluded) arteries, and a high restenosis rate. The restenosis problems have improved with the use of coronary stents[8-10]. However, procedural success rates have only shown modest improvement in the past 20 years from 50-60% in the 1980's[11,12] to 60-70% range in the 1990's[5,13-15], due to some improvements in angioplasty equipment, such as hydrophilic guide wires[16,17]. In contrast, PCI enjoys success rates in excess of 95% in stenotic but non-occluded arteries. In fact, success rates of 70% is probably an overestimation of PCI success for CTO, since attempts are generally only made in lesions felt to have a reasonable chance of success. Several lesion characteristics have been identified that are predictors of procedural success and influence the decision to proceed with angioplasty. Duration of occlusion, which is often difficult to ascertain, is a major predictor. In instances where this can be reliably estimated, recent coronary occlusions (i.e. <3 months duration) have been reported in two studies to be successfully dilated in 74% and 89% of cases[5,13]. However, if the occlusion duration exceeds 3 months, success rates decline to 59% and 45%, respectively. Other variables that are predictive of procedural failure include long lesion length of the occluded segment (>15 mm)[1,18,19], presence of bridging collaterals, absence of a tapered funnel leading into the occluded segment and possibly smaller vessel size[20]. Failure rates are also higher in absolute occlusions (no distal opacification) than in functional total occlusions (subtotal occlusion with faint late anterograde opacification of the distal segment without discernible continuity)[6,19,21].

Why Do PCI Fail in Chronic Total Occlusions?

Inability to cross the CTO with a guide wire is the overwhelming reason for PCI failure, accounting for >75% of failures[5,19]. Recent technical innovations with newer types of guide wires designed specifically for total occlusions such as the Magnum™ wire[22], the low speed rotational angioplasty device[23,24] and excimer laser powered guide wire (Prima™ Total Occlusion Device)[25-27] have not improved success rates compared to conventional guide-wire techniques[28,29]. Thus a purely mechanical approach of designing stiffer and more powerful guide wires to try and push through fibrotic total occlusions has only limited efficacy. Although thrombolytic therapy is effective in acute coronary occlusions, only a small number of native artery chronic occlusions have been treated with prolonged thrombolytic infusions with limited results[30,31], and this strategy has largely been abandoned. There are no other published reports of pharmacologic treatments of chronically occluded arteries in order to improve angioplasty results.

Why Should CTO be Opened?

The myocardial territory supplied by a chronically occluded artery may still be viable, particularly in the situation of a slowly developing occlusion that is associated with extensive collateralization. Myocardial ischemia is a common sequelae of CTO since the blood flow through collaterals is inadequate in situations of increased myocardial demand (exercise, post-prandial, stress). Consequently, significant angina pectoris represents the most common cause of attempted PCI in the setting of CTO. The situation of inadequate blood supply to viable myocardium (termed "hibernating myocardium") is also a major cause of potentially reversible myocardial dysfunction leading to heart failure. Moreover, there is accumulating data that CTO portend a poorer prognosis. A higher 2-year adjusted mortality rate has been reported in patients with a total occlusion compared with patients with subtotal occlusions[32]. In patients with single-vessel disease followed for a mean of 4 years, a significantly higher rate of sudden death (15%) occurred in patients with CTO than in patients with high grade stenosis (3%)[33]. Recent data has shown that revascularization of CTO improves left ventricular function (the main determinant of heart failure) and possible long-term mortality[34-38]. Suero and colleagues demonstrated a significant increase in 10-year survival for successful CTO treatment compared with failed CTO treatment (73.5% vs 65.1%)[7]. The survival benefit of an open artery may be due to enhanced electrical stability of the myocardium with reduction of ventricular tachyarrhythmias, absence of late potentials and the preservation of vagal tone[53-55].

Experimental Use of Matrix Metalloproteinases:

Collagenase formulations have been used in in-vitro cell culture studies for a long period of time. These formulations act to isolate cells from tissue by degrading the surrounding matrix and these cells are then used for cell culture. There are very few reports of using collagenase formulations for in-vivo studies. An experimental model of intracerebral hemorrhage in rats has been developed by systemically infusing bacterial collagenase (type XI and type VII) or a combination of collagenase and heparin directly into the caudate nucleus[48-50]. In this model, erythrocytes accumulate around large caudate blood vessels 10 minutes after injection with extensive bleeding present at 4 hours, presumably due to degrading interstitial and basement membrane collagen in the thin-walled intracerebral vessels[49].

Kerényi and colleagues[51] have previously reported on using several different enzymes including collagenase in a rabbit atherosclerotic model. These enzymes were delivered through a double balloon catheter in which two balloons are inflated and the enzyme is injected into the space between the two inflated balloons. These enzymes were left for a maximum of 30 minutes and then the arteries were immediately removed. In this model, rabbits were fed a high cholesterol diet, which resulted in the development of modest atherosclerotic plaques that were minimally stenotic (approximately 30%) and therefore not occlusive or a barrier to passing a guidewire or angioplasty balloon catheter. Release of various enzymes (trysin or papain alone or in combination with collagenase) frequently resulted in not only dissolution of the plaques but also caused extensive damage to the media of the artery. Collagenase by itself had little effect. These studies support the rationale for using collagenase to degrade extracellular matrix within the vessel wall but also caution about the potential limitations of such a therapy with high doses, particularly in thin-walled arteries.

Thus, although there is some experimental basis to support the use of the matrix degradative properties of collagenase for atherosclerotic plaques in general, chronic total arterial occlusions are a unique manifestation of the atherosclerotic disease. Moreover, none of these studies address the unique clinical situation of a chronically occluded artery in which a long segment of artery is completely occluded and will not permit the passage of guide wires which are an absolute requirement for performing balloon angioplasty and stenting. In addition, the parameters of a successful therapeutic approach in this specific setting (chronic total occlusions) such as the exact enzyme composition and amount, local delivery strategy and appropriate incubation period of the enzymes prior to attempting guidewire crossing are unknown.

Experimental studies of chronically occluded arteries have been limited by the lack of a suitable animal model. Hyo-Chun Yoon et. al published a disclosure of a porcine animal model of a chronic peripheral arterial occlusion in the Journal of Interventional Radiology, January-February 1996 at pages 65-74. The model presented one month old and three month old occlusions. There was significant variation in the degree of organization within the occlusions. Infusion therapy with collagenase and urokinase were attempted, but patentcy was not restored in any animal and attempts at the passage of a guide wire through the occlusion were unsuccessful. Collagenase used after urokinase thereapy was indescriminate in its digestion of the native vessel and the organized thrombus. Yoon et al. summarized in their results that neither urokinase nor collagenase proved effective against chronic clot in the doses and time course studied with their porcine model.

Several issued patents have included some claims for the use of collagenase or other matrix degrading enzymes to reduce the amount of atherosclerotic plaque in a blood vessel. In U.S. Pat. No. 6,025,477, Calendoff teaches a method of directing enzymes to the atherosclerotic plaque through binding a proenzyme(s) [fibroblastic collagenase, gelatinase, polymorphonuclear collagenase, granulocytic collagenase, stromelysin I, stromelysin II or elastase] to a reagent (preferably a bifunctional antibody) that binds specifically to the atherosclerotic plaque to form a reagent-plaque complex (column 16; lines 61-66). The proenzyme, which is also bound to the reagent would then be activated by cleavage and be converted into an enzyme capable of dissolving a component of the plaque (column 42, lines 19-32).

In U.S. Pat. No. 5,811,248 (Ditlow) and U.S. Pat. No. 6,020,181 (Bini), similar methods of targeting delivery of matrix degrading enzymes to atherosclerotic plaques have been taught. Ditlow teaches a method of using a reagent comprising CDR-grafted antibody or fragment conjugated to an enzyme capable of digesting atherosclerotic plaque (column 5, lines 11-15). Bini teaches a method of binding fibrinolytic matrix metalloproteinases to moieties having specificity for a biological target molecule such as an antibody that would be preferentially directed to a fibrin(ogen) substrate for improving fibrin(ogen)olytic efficacy (column 14, lines 1-10). However, these methods of enzyme delivery would likely only be relevant for non-occluded arteries, particularly for generalized atherosclerosis disease. These teachings would not be applicable to the specific setting of performing angioplasty in occluded arteries, which receive very little circulating blood flow due to the complete occlusion. In this setting, much higher concentrations of enzymes are required which can only be achieved through a localized delivery system. Moreover, the exact parameters of the delivery and amounts of these enzymes must be optimized to ensure adequate alteration of the composition and substance of the occlusive plaque without damaging the outer layers (media and adventitia) of the arterial wall. In U.S. Pat. No. 6,020,181, Bini teaches a method of causing the degradation of fibrin (ogen) by means of fibrinolytic matrix metalloproteinases, preferably MMP-3 or MMP-7. This patent is relevant to acute arterial occlusions, which contain abundant thrombus and fibrin and are responsible for acute myocardial infarctions and sudden death. The method can be performed in vivo as a method of thrombolytic therapy in which a fibrinolytic matrix metalloproteinase is administered to a subject to degrade thrombus in situ. However, this application of the fibronolytic matrix metalloproteinase is not relevant to the problem of performing angioplasty in chronically occluded arteries, which contain extensive collagen and other extracellular matrix components and very minor amounts of fibrin or fibrinogen. In addition, as stated above, the systemic delivery method is not relevant to local delivery into arterial occlusions.

In summary, CTO remain an important subset of PCI lesions with quite limited success, predominantly due to inability of crossing the occlusion with a guide wire. The fibrotic, collagen-rich characteristic of these plaques is the underlying impediment to passing a guide wire. The vast majority of patients with symptomatic chronic total occlusions are either treated by medical therapy with often limited effectiveness or undergo invasive bypass surgery. In addition to causing significant angina, there is strong evidence that CTO are also associated with poorer left ventricular function and possibly worse survival than stenotic (but not occluded) lesions or successfully dilated chronic occlusions. Stenting of CTO has significantly improved long-term patency, which was the other limitation of angioplasty. Thus, the current evidence suggests that opening total occlusions by percutaneous interventions is underutilized and necessitates new approaches.

There is a need for a method of treatment of the plaque to facilitate guidewire passage through the occlusion as a prerequisite for successful angioplasty. More particularly, there is a need to chemically alter the collagen content and structure in these occlusive fibrous plaques to facilitate crossing with conventional guide wires.

There is a further need for an animal model of chronic total arterial occlusion to facilitate research and development methods treating chronic arterial occlusions which cannot be crossed by a conventional angioplasty guide wire.

SUMMARY OF THE INVENTION

The use of a collagenase containing formulation has been identified for degrading collagen within an occlusive atherosclerotic plaque in a chronically occluded animal tube or cavity. More particularly, a collagenase containing formulation is used as an infusion preparation for administration and retention of a therapeutic dosage of collagenase adjacent to or into the atherosclerotic plaque during a formulation exposure waiting period.

A medical-related apparatus is provided for degrading collagen within an occlusive atherosclerotic plaque in a chronically occluded animal tube or cavity comprising a medical-related device having provided thereto a therapeutic amount of a collagen degrading composition comprising a proteiolytic enzyme containing formulation.

A method of is provided for treating chronically occluded animal tubes and cavities. The first step in the method is administering a therapeutic effective amount of a proteolytic enzyme-containing formulation adjacent to an occluding atherosclerotic plaque. There follows a pre-angioplasty waiting period prior to crossing the plaque with an angioplasty guide wire. Following the waiting period, the plaque is crossed with an angioplasty guide wire.

BRIEF DESCRIPTION OF THE DRAWINGS

Preferred embodiments of the invention have been chosen for purposes of illustration and description, but are not intended in any way to restrict the scope of the present invention. The preferred embodiments of certain aspects of the invention are shown in the accompanying drawings, wherein:

FIG. 1 shows pathology of a chronically occluded rabbit femoral artery (12 weeks duration). M=media, A=adventita, A,B=Movat, 10× original; C=Movat, 20×; D=Hematolylin and Eosin 20×. A shows the lumen (L) is occluded by fibrotic intimal lesion. B shows the occluded lumen also contains small vascular channels. C shows magnification of small vascular channels (indicated by arrow). D shows fibrotic and cellular components of the occluded lumen (L).

FIG. 4A shows successful wire crossing (region filled by red blood cells) in collagenase treated artery (450 µg). Evidence of some plaque digestion is evident. Internal elastic lamina (arrow) and medial layer remain intact.

FIG. 4B shows placebo treated artery with unsuccessful wire crossing. An extensive and occlusive intimal plaque (P) is present.

An extensive and occlusive intimal plaque (P) with microvessels is present. Part of the media (between 3 o'clock and 5 o'clock) has been degraded and atrophied.

Figure 6:
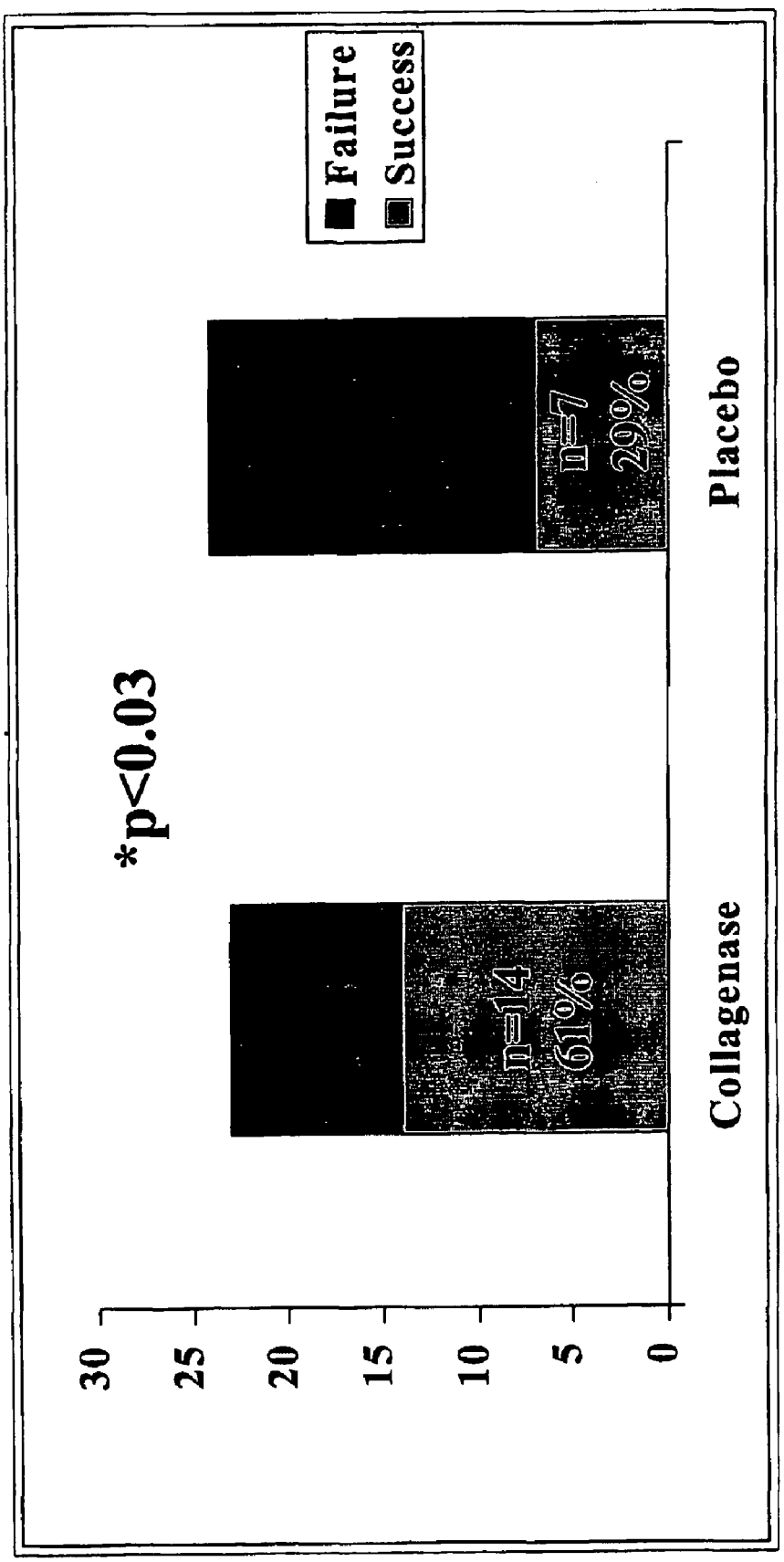

FIG. 6 shows statistical significant differences ($p<0.03$) in successful guide wire crossings in collagenase treated compared to placebo treated arteries at 72 hours after treatment. The treatments were randomized and the operator was blinded to the treatment allocation.

Figure 7:

FIG. 7 shows a Western blot analysis for interstitial collagenase (MMP-1) in collagenase and placebo-treated arteries at 24 hours after treatment. Chronic arterial occlusions that undergo either treatment showed the presence of a band at ≈93 kD, confirming the presence of interstitial collagenase (MMP-1). This band was markedly increased in the collagenase-treated arteries (lanes 1 and 2) compared to the placebo-treated arteries (lanes 3 and 4), showing increased interstitial collagenase protein in collagenase-treated arteries. Lane 5 shows the presence of MMP-1 protein in the collagenase formulation and was run as a positive control.

Figure 8:
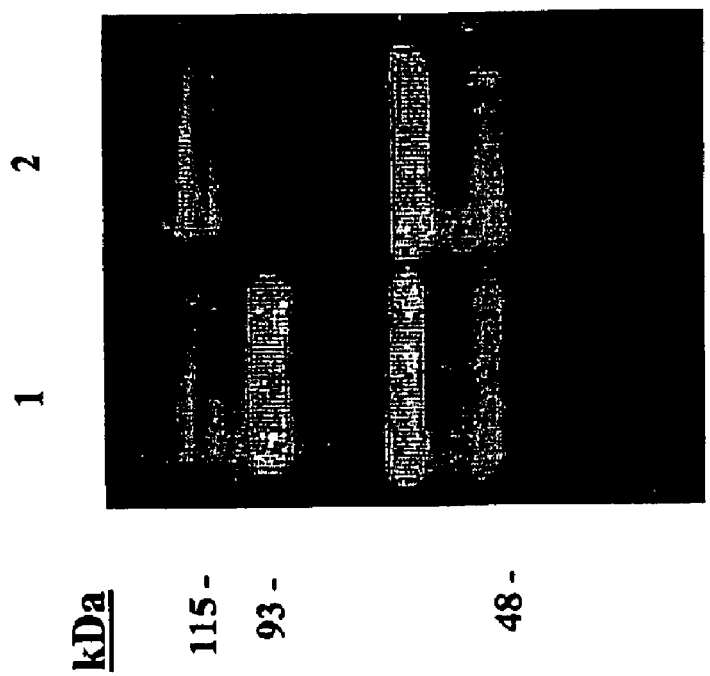

FIG. 8 shows a gelatin zymogram from a collagenase treated artery (lane 1) and placebo treated artery (lane 2) at 24 hours after treatment in chronically occluded arteries. There was an increase of an 92-kD gelatinase (MMP-9) only in collagenase-treated arteries with no MMP-9 activity found in placebo-treated arteries. Lytic bands were present at 92 and 82 kD, reflecting both the proenzyme and the activated forms of MMP-9 in collagenase-treated arteries. Both collagenase and placebo-treated arteries also had evidence of a 72-kD gelatinase (MMP-2).

Figure 9:
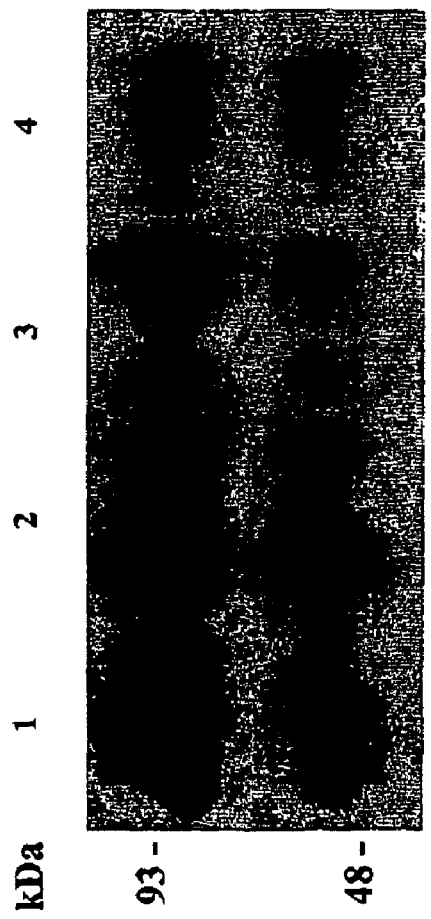

FIG. 9 shows a Western blot analysis for degraded collagen fragments (carboxy terminus of collagen fragments) at 24 hours after treatment with either collagenase (lanes 1 and 2) or placebo (lanes 3 and 4) in chronically occluded arteries. There was a marked increase in collagen fragments in collagenase treated arteries.

FIG. 10 shows effects of collagenase and placebo treatment at 24 hours in the absence of attempts to cross with guide wires. Movat 10× original, P=intimal plaque (that occludes lumen), M=medial layer, Ad=adventitial layer. A A shows collagenase treated artery with extensive plaque digestion within the previously occluded lumen (L). Internal elastic lamina (arrow) and medial layer remain intact. B shows placebo treated artery with an extensive and occlusive intimal plaque (P) with microvessels is present. There is also quite extensive disruption of the internal elastic lamina (indicated by arrow) and medial atrophy during the chronic remodeling after occlusion. The placebo treated arteries had identical pathology to the arteries previously described in the chronic total occlusion model.

DETAILED DESCRIPTION OF THE INVENTION

In accordance with the present invention, an approach to significantly improve the procedural results of chronic occlusions is described. A method of local delivery of a therapeutic effective amount of a proteolytic enzyme-containing formulation having a matrix-degrading enzyme, belonging to the family of matrix metalloproteinases, serine elastases, trypsin, neutral protease, chymotrypsin, aspartase, cysteinase and clostripain, can effectively alter the matrix content of the occluding plaque in a way that significantly facilitates guide wire crossing and substantially improves procedural success rates, without causing adverse effects of these enzymes on medial layers of the occluded artery and in adjacent non-occluded arterial segments.

Pathology of Chronic Total Occlusions in Human Coronary Arteries

The underlying atherosclerotic plaques in CTO are predominantly fibrocalcific[39], consisting of smooth muscle cells, extracellular matrix and calcium and variable amounts of intracellular and extracellular lipids[40]. Inflammatory cells are commonly seen[39]. Collagens are the major structural components of the extracellular matrix, comprising up to 50% of the dry weight[41,42], with predominance of types I and III (and minor amounts of IV, V and VI) in the fibrous stroma of atherosclerotic plaques[43,44]. In CTO of less than 1-year duration, proteoglycans are also commonly found in the intima. Thrombus formation contributes to a varying degree, depending on the severity of the underlying atherosclerotic plaque, and can result in single or multiple layers of clot. Over time, the thrombus becomes organised and converted into a collagen-rich fibrous tissue (known as fibrointimal hyperplasia), which eventually is incorporated into the underlying atherosclerotic plaque[40]. The most recently developed fibrointimal hyerplasia is the most likely structure that the angioplasty guide wire must traverse in order to cross the total occlusion. Older organized collagen-rich fibrous tissue is the barrier to successful crossing with current angioplasty techniques. The presence of the most recently formed fibrous tissue within the lumen is the target of the collagenase therapy of the present invention. Intimal plaque neovascular channels are also common in CTO (>75%), regardless of the occlusion duration[39]. The formation of several new channels through the occlusion (intra-arterial arteries), and/or dilation of the vasa vasorum (i.e. bridge collaterals), provides a vascular supply through the occluded segment for transportation of nutrients and potential agents such as collagenase. However, these small channels are not sufficient to provide adequate distal coronary perfusion to prevent symptoms.

The present invention is directed to a method of treating chronically occluded animal tubes and cavities. The phrase "animal tubes and cavities" refers to both human and other animal species, in that the methods of the present invention have both medical and veterinary applications. Moreover, the methods of the present invention may be applied to occluded tubes and cavities that contain fibrotic collagen-rich tissue such as root canals, fallopian tubes, bile ducts, sinuses, ureters and urethras, arteries, veins and vein grafts used for arterial conduits. The methods taught herein were primarily developed with regard to the occlusion of coronary arteries, but can be used for occluded noncoronary arteries such as iliac arteries, popliteal arteries, femoral arteries, carotid arteries or subclavian arteries. Routine adaptation of the methods taught herein are contemplated for application to occluded bodily tubes and cavities including veins, vein grafts, root canals, fallopian tubes, bile ducts, sinuses, ureters and urethras.

Animal Model

The present invention represents a previously unattempted approach to the treatment of chronically occluded arteries that are not amenable to angioplasty since the lesions cannot be crossed by a guidewire. Experimental models of uniformly organized collagen-rich chronic occlusions have not been previously readily available. The unique properties of chronic occlusions that have made them heretofore difficult to cross include the high collagen content and the length of the occlusion that limit direct contact of parts of the occlusion to therapy. In order to assess the effects of collagenase, an in-vivo chronic total occlusion animal model was developed (FIG. 1) in accordance with the present invention. The animal model can be established with reference to any typical laboratory testing animal, including but not limited to, rabbits, pigs, dogs, sheep, rats and non-human primates. Dosages and times may require adjustment to account for variations in species and body size. For illustrative purposes, the animal model of the present invention will now be described with respect to Male New Zealand white rabbits, weighing 3.0-3.5 kg.

The first step in the method is isolating an arterial segment of an animal artery (such as the femoral artery illustrated in FIG. 1) and stopping blood flow with occlusive ligatures in the isolated arterial segment of an animal artery. This step is accomplished in the preferred embodiment of the present invention, by anesthetizing the male rabbits with isofluorane, and then making incisions below the inguinal ligament bilaterally. Ligatures are then placed at least about 5 mm apart to isolate a segment of femoral artery. In the preferred embodiment, the ligatures were placed about 15 mm apart. The ligatures not only isolate, but also physically occlude the arterial segment.

The next step in the method is injecting topical thrombin into the arterial segment to form an acute thrombotic occlusion. This step can be carried out by using a 27-gauge needle to inject 100 IU of bovine thrombin solution (Thrombostat™, Parke-Davis) into the isolated arterial segment. After a waiting period of at least 20 minutes the sutures were loosened to determine if an occlusion has formed. This is accomplished by loosening the ligatures (typically sutures) to determine if an whether anterograde blood flow was still present. If anterograde blood flow is still present, one or two additional thrombin injections are performed using the same technique until an acute occlusion is created. Typically, the ligatures are applied for total of 60 minutes and then removed.

A waiting period follows during which the acute thrombotic occlusion is converted into a chronic fibrotic occlusion. The waiting period is of a duration between about 10 weeks and 25 weeks. In order to determine the appropriate waiting period, the arterial patency is assessed by angiography (using the left carotid artery for arterial access) at a mean duration of 16 (±4) weeks.

It is believed that the present method of developing in-vivo animal models of chronic occlusions can be adapted to other bodily and cavities that contain fibrotic collagen-rich tissue such as root canals, fallopian tubes, bile ducts, sinuses, ureters and urethras, veins and vein grafts. The method would comprise the steps of isolating a segment of the selected animal tube, and stopping fluid flow through the tube with occlusive ligatures placed at least about 5 mm in the isolated segment of an animal tube, then injecting a topical sclerosing agent (such as tetracycline or other agent appropriate to the selected cavity or tube) into the segment to form an acute occlusion; and, waiting while the acute occlusion is converted into a chronic fibrotic occlusion.

Pathology of Chronic Total Occlusion Model

In the first 2 rabbits (at 10 and 15 weeks) that demonstrated persistent occlusion of the femoral arteries, the arteries were removed and examined pathologically to confirm that the histologic features of a chronic occlusion had developed. There was minimal to absent fibrin remnants evident in the chronic, fibrotic occlusions (FIG. 1). In addition to mature fibrous tissue, there were multiple small intraluminal vascular channels and occasional extracellular lipid deposits, pigment-filled macrophages, and lymphocytes. There was no evidence of vascular calcification and or inflammation in the medial layer. The occluded segments had also undergone substantial inward remodelling compared to the adjacent patent arterial segments. A common feature in the chronic occlusion model was disruption of the internal elastic lamina at several sites with intervening fibrous tissue. All of these changes are analogous to the chronic human coronary artery total occlusion.

This model features a number of therapeutic challenges. The average occlusion length was approximately 28 mm (range 14 mm-56 mm), which is substantially longer than most clinical coronary occlusions, upon which percutaneous coronary interventions would be attempted. Also, the occluded lumens and overall vessel size were quite small due to the inward remodelling.

Method of Treating Chronically Occluded Animal Tubes and Cavities

Reference is made in the present description and claims to a "proteolytic enzyme containing formulation". The present invention contemplates that the proteolytic enzyme is selected from the group consisting of matrix metalloproteinases, serine elastases, trypsin, neutral protease, chymotrypsin, aspartase, cysteinase and clostripain. Matrix metalloproteinases (MMPs) are a group of zinc-containing enzymes that are responsible for degradation of extracellular matrix (ECM) components, including fibronectin, collagen, elastin, proteoglycans and laminin. These ECM components are important components of the occluding atherosclerotic plaque. MMPs play an important role in normal embryogenesis, inflammation, wound healing and tumour invasion[45,46]. These enzymes are broadly classified into three general groups: collagenases, gelatinases and stromelysins. Collagenase is the initial mediator of the extracellular pathways of interstitial collagen degradation[47], with cleavage at a specific site in the collagen molecule, rendering it susceptible to other neutral proteases (e.g. gelatinases) in the extracellular space. It is preferred that the proteolytic enzyme containing formulation comprises a matrix metalloproteinase selected from the group consisting of collagenase, type 1A collagenase, gelatinases, and stromelysins. It is most preferable that the proteolytic enzyme containing formulation comprises collagenase, whether alone or in combination with other enzymes. It should be understood that the references to the use of a "collagenase formulation" in this description are intended to be illustrative of the preferred embodiment of the present invention, but are not intended to be limiting.

The method of treating chronically occluded animal tubes and cavities, such as coronary arteries that can not be crossed by conventional angioplasty guide wires (0.014" or 0.018" diameter) (FIG. 2A) comprises the steps of administering a therapeutic effective amount of a proteolytic enzyme containing formulation adjacent an occluding atherosclerotic plaque, waiting for a pre-angioplasty waiting period prior to crossing the plaque with an angioplasty guide wire, and then crossing the plaque with an angioplasty guide wire.

Figure 2:
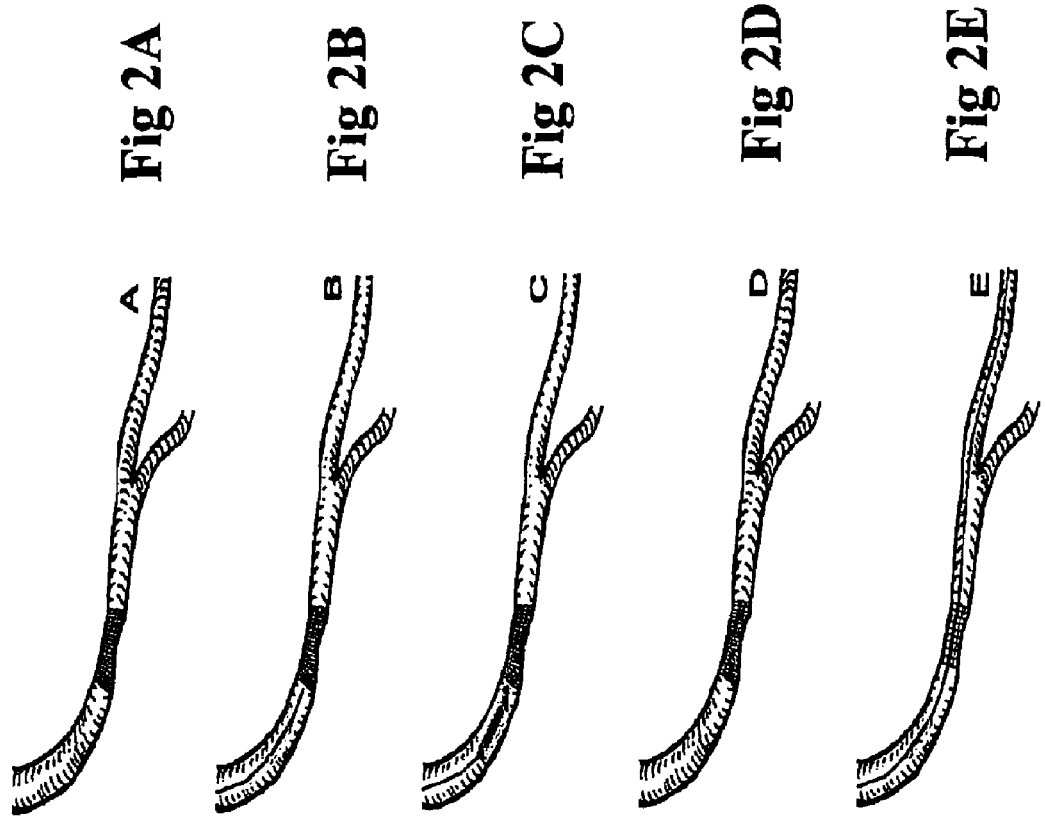
FIG. 2 shows an embodiment of the method of treating chronically occluded tubes and cavities according to the present invention. A shows the chronic total arterial occlusion. B shows failure of 2 different guide wires (Choice PT™ and Wizdom™) to cross the occlusion using an over-the-wire angioplasty balloon catheter. C shows an inflated angioplasty balloon catheter just proximal to the total occlusion. The guide wire has been removed from the wire port of the angioplasty balloon catheter and collagenase has been infused into the small space between the inflated angioplasty balloon (to prevent proximal run-off) and the occluded arterial segment. D shows the collagenase solution diffusing along the arterial occlusion and degrading part of the occluded segment. E shows the guide wire successfully crossing the arterial occlusion at 72 hours after placement of the collagenase. The occlusive arterial segment has been partially degraded by the collagenase allowing the guide wire to cross through the true lumen of the artery into the non-obstructed artery beyond the arterial occlusion.

The step of administering a therapeutic effective amount of a proteolytic enzyme containing formulation is conducted as follows. After determining that a coronary artery is totally occluded by angiography, an over-the-wire angioplasty balloon catheter is advanced on a guide wire into the occluded coronary artery using fluoroscopic guidance. If the occlusion cannot be crossed with conventional 0.014" or 0.018" coronary angioplasty guide wires (FIG. 2B), the wire is removed. The angioplasty balloon is inflated at low pressure, in the range of between about 1 to 5 atmospheres, to prevent proximal run-off of the collagenase formulation during administration. An inflation of the angioplasty balloon to a pressure of about 4 atmospheres is preferable (FIG. 2C). A collagenase-containing formulation is slowly infused into the small space between the inflated balloon and the occlusion. As illustrated in FIG. 2C, the collagenase-containing formulation is being infused directly through the wire port of the angioplasty balloon catheter. The infusion is performed under a pressure in the range of about 0.5 atmospheres to 3.5 atmospheres. It is preferable for the infusion to occur at a low pressure of between about 1 and 2 atmospheres. The formulation may also be infused directly into the proximal part of the occlusion itself through an infusion needle or a catheter.

After the infusion, the collagenase containing formulation is retained in position by the inflated angioplasty balloon for a formulation exposure waiting period of between about 10 and 100 minutes. The waiting period is preferably within the range of about 50 to about 80 minutes. In accordance with the preferred embodiment, the formulation exposure waiting period is about 60 minutes, after which the angioplasty balloon is deflated and then removed. (FIG. 2D)

It has been found that an effective therapeutic amount of proteolytic enzyme containing formulation comprises about 50-2000 µg of type IA Collagenase.

After administration of a therapeutic effective amount of the proteolytic enzyme containing formulation and after the angioplasty balloon is deflated and then removed, a pre-angioplasty waiting period of between about 1 and 108 hours is needed. It has been found that a waiting period of between about 12 hours and about 86 hours is preferable, with the best results occurring after a waiting period of about 72 hours. The waiting period is required for the enzyme containing formulation to diffuse along the length of the occluded segment and to sufficiently degrade the collagen and "soften" the occluding plaque.

If the arterial wall (medial) collagen is as vulnerable to this therapy as the plaque collagen that occludes the lumen, then the collagenase dose will either be too low to be efficacious or too high to avoid excessive damage and weakening of the arterial wall. However, newly formed collagen within the occlusive plaque is the most vulnerable to the effects of matrix metalloproteinases. The collagen in the normal arterial medial layer forms early in the development of the vessel wall and is extensively cross-lined with very slow turnover. By contrast, intimal plaque development which occurs an effect of the organisation of occlusive thrombus is a very dynamic process that contains more recently synthesized collagen with variable cross-linkage and susceptibility to enzymatic degradation by MMP's such as collagenase. The most recently organised thrombus is the most likely part of the lesion that the angioplasty guidewire can traverse in order to cross the total occlusion. Thus, this recently formed, relatively loose fibrous tissue within the lumen is the principal target of the therapy methods of the present invention. At 72 hours, the patient returns to the catheterization laboratory and the operator again attempts to cross the total occlusion with conventional angioplasty guide wires which is then followed by an angioplasty (FIG. 2E).

A number of in-vitro and in-vivo studies have been performed to assess the feasibility and efficacy of the therapy. The studies have been done with Type IA Collagenase (Sigma), a commercially available bacterial collagenase formulation obtained from the fermentation of *clostridium histolyticum*. This enzyme formulation is generally used to isolate cells from tissue specimens for cell culture. This formulation also contains small amounts of clostripain, neutral protease and trypsin-like activities. Type IA Collagenase (Sigma) is a bacterial collagenase formulation that is obtained from the fermentation of clostridium histolyticum. The range of doses were based on the results of an in-vitro assay which assessed the effects of a range of doses and incubation periods of the collagenase formulation on the arterial wall structure. Human coronary arteries containing stenotic atherosclerotic plaque were obtained at autopsy. Arterial segments were cut into 3 mm cross-sections and mounted on agar gels in a culture well. This enabled selective delivery of collagenase directly into the lumen with a fine pipette. Thus only the occlusive plaque was in direct contact with the collagenase formulation, similar to the in-vivo approach of intraluminal delivery of the collagenases. After incubation period of 4 hours and 18 hours, it was shown that doses of 100-500 μg/ml of Type IA collagenase caused definite in-vitro degradation of the occluding plaque, although there was some damage to the deeper layers of the vessel wall at the upper dose range.

After confirming persistence of the occlusion, an over-the-wire angioplasty balloon catheter (3.0 mm diameter) was advanced through a 5F sheath in the left carotid artery and fluoroscopically guided into the iliac artery proximal to the occluded femoral artery. An attempt was made to cross the occlusion with two conventional 0.014" coronary angioplasty guide wires [Wizdom™, (Cordis) and Choice PT™, (Boston Scientific)]. If the operator was unable to cross with the guide wires, lesions were entered into the study. The angioplasty balloon catheter was then advanced to the occlusion and the occlusion length was measured using the known balloon length (20 mm between markers) as a scaling device. The balloon was inflated to 4 atmospheres to prevent proximal run-off of the enzyme solution. The guide wire was then removed and the wire port was used to administer a 1.5 ml solution containing either Type IA Collagenase (n=33 arteries, total dose 100-450 μg) or placebo (n=24 arteries). The enzyme formulation was delivered slowly at 1-2 atmospheres.

The angioplasty balloon was left inflated for a period up to 60 minutes. Initial attempts to cross the chronic occlusions (n=10) within 1 hour of completion of the collagenase administration were all unsuccessful. All other attempts were done 72 hours after administration of either collagenase (n=23) or placebo (n=24). After 1 of the initial 2 collagenase-treated arteries were successfully crossed at 72 hours, the remaining arteries (n=45) were randomized to either placebo or collagenase treatment without the knowledge of the operator. The attempt to cross the occlusion at 72 hours was made after accessing the arterial circulation through a right carotid cutdown and placement of the angioplasty balloon catheter as described above. Frequent injections of contrast were performed to assess the distance crossed with the angioplasty guide wires (Wizdom™ and Choice PT™) and to ensure the guide wire remained in the true lumen. Attempts at wiring were continued until the lesion was crossed, a large dissection was created, or when no further progress could be made on multiple attempts with different wires. Successful crossing of the lesion was identified angiographically by free movement of the wire tip in the distal vascular bed beyond the occluded segment. After wire crossing, no angioplasty was performed so that the arterial architecture would be left intact for analysis. At the end of the procedure, the rabbits were killed and the femoral arteries were then dissected out and sent for histological analysis (Movat and H&E). At least 3 cross-sections were examined per occluded segment.

Statistics

A Fisher exact test was used to assess differences in the rates of successful crossing of occlusions with a guide wire. A p value <0.05 was considered statistically significant.

Occlusion Lengths

There were no significant differences in occlusion length between collagenase-treated arteries (29.5+/−8.6 mm) and placebo-treated arteries (27.9+/−8.7 mm).

Figure 3:
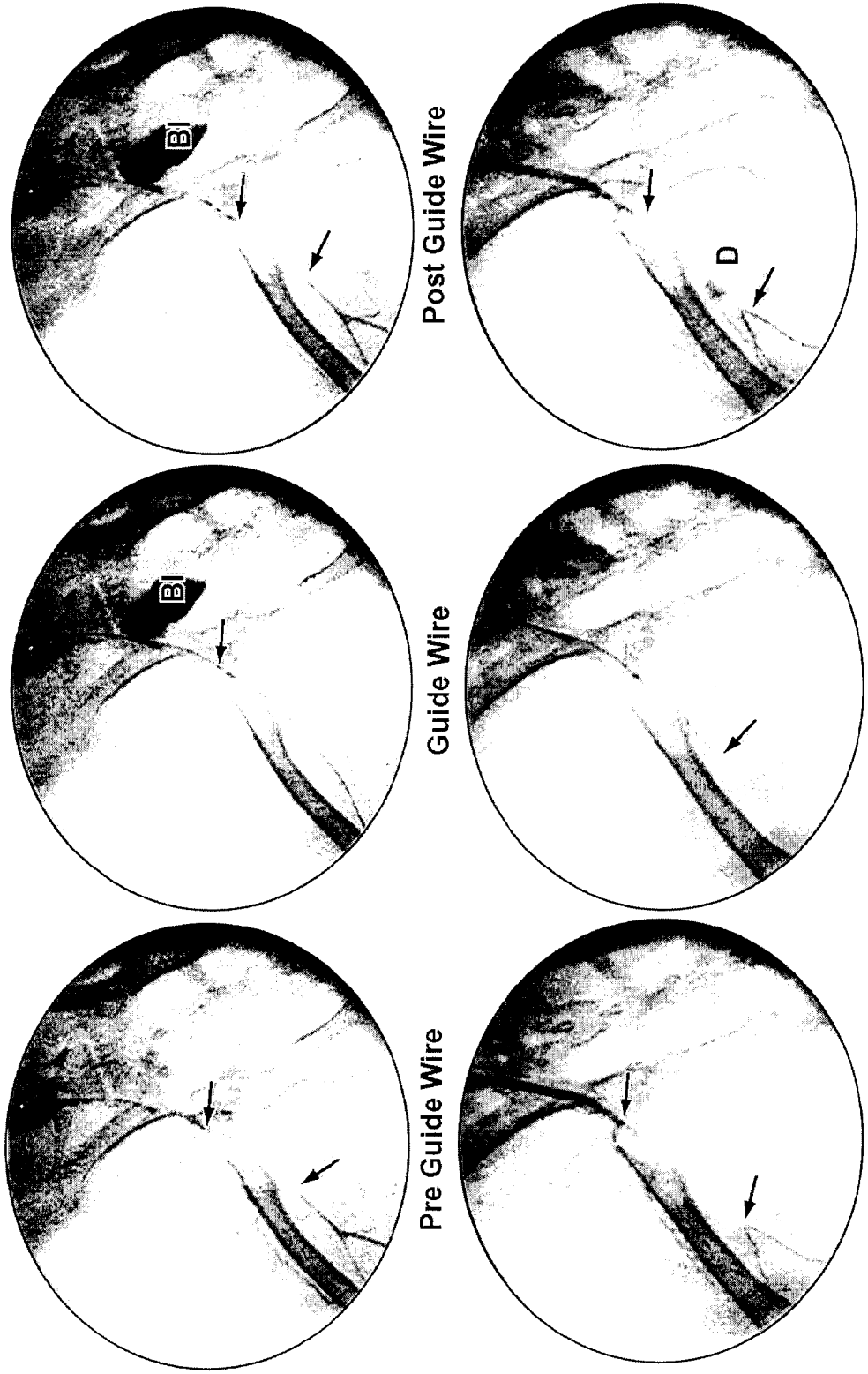
FIG. 3 shows angiographic results of wire crossing attempts in the rabbit femoral artery chronic total occlusion model. A-C Successful attempt at 72 hours after collagenase infusion. D-F: Unsuccessful attempt at 72 hours after placebo infusion. BI=contrast in bladder. A shows the occlusion is evident between the two arrows in the angiogram prior to the guide wire attempt in collagenase treated artery. B shows the guide wire (indicated by arrow) has successfully crossed the occlusion. C shows that after the crossing with the guide wire there is no evidence of dissection. D shows the occlusion is evident between the two arrows in the angiogram prior to the guide wire attempt in placebo treated artery. E shows that the guide wire (arrow) cannot be advanced across the occlusion. F shows contrast extravasation from guide wire dissection (D) is evident in unsuccessful attempt to cross the total occlusion. 4 Guide wire crossing at 72 hours after collagenase infusion. Movat 10× original, P=intimal plaque (that occludes lumen), W=site of wire crossing, M=medial layer, Ad=adventitial layer.
Figure 5:
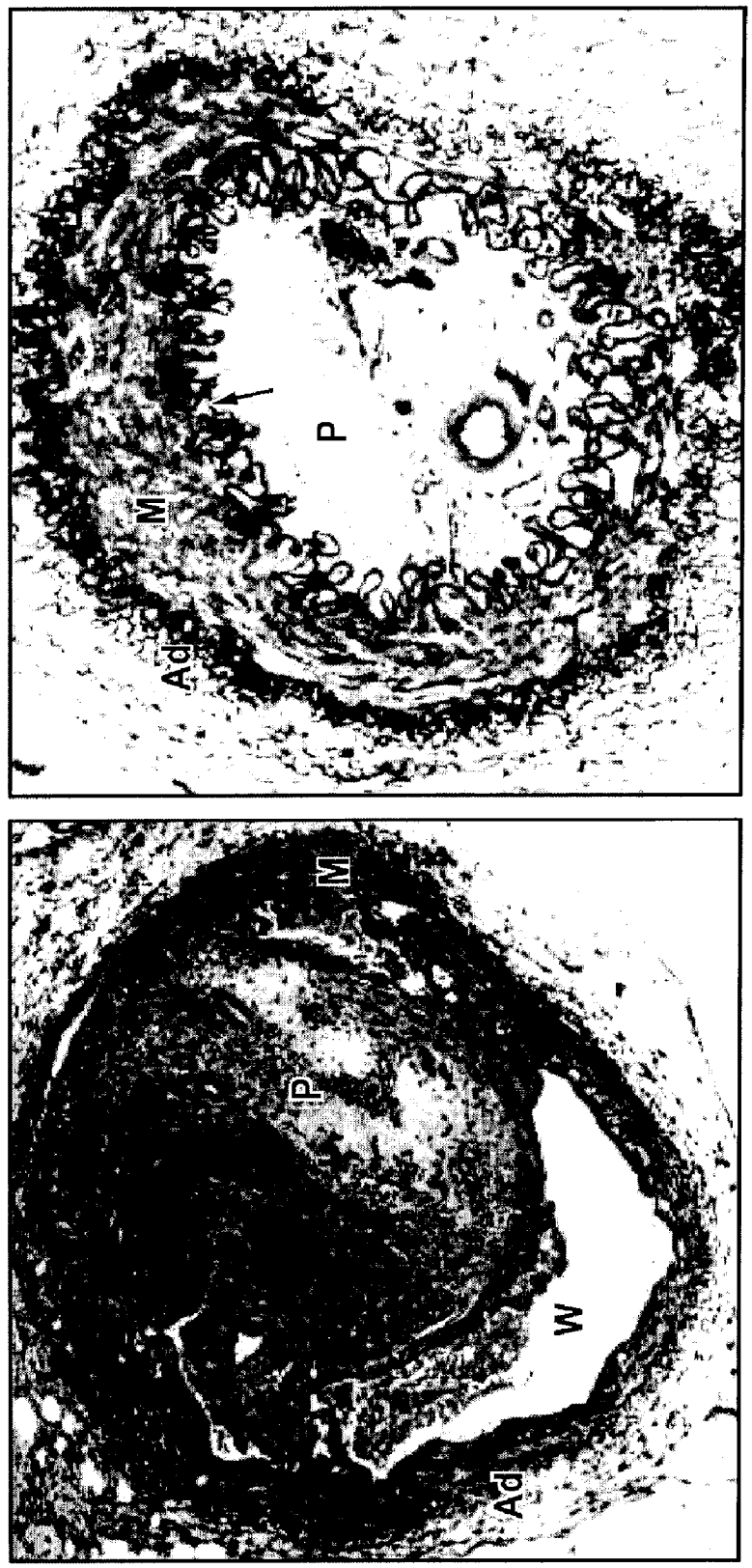
FIG. 5 Guide wire crossing at 72 hours after collagenase infusion. Movat 10× original, P=intimal plaque (that occludes lumen), W=site of wire crossing, M=medial layer, Ad=adventitial layer. A shows successful wire crossing (region filled by open space and red blood cells) in collagenase treated artery (450 µg). Evidence of some plaque digestion is evident. Internal elastic lamina (arrow) and medial layer remain intact. B shows placebo treated artery with unsuccessful wire crossing.

Angiographic Success Rates in Crossing Chronic Occlusions at 72 Hours:

There was a significant (p<0.03) increase in successful guidewire crossings in collagenase-treated arteries (14/23, 61%) compared to placebo-treated arteries (7/24, 29%) (FIGS. 3 and 5).

TABLE 1

| Treatment | Incubation Time | Success/Attempts | % Success |
|---|---|---|---|
| Collagenase | 1 hr | 0/10 | 0% |
| Collagenase | 72 hr | 14/23 | 61% |
| Placebo | 72 hr | 7/24 | 29% |

Pathology of Arteries After Crossing Attempts:

In cases where angiography showed successful guide wire crossing, histology confirmed the presence of blood-filled vascular channels where the guide wire traversed the occlusive intimal plaque (FIGS. 4A and 5A). There was also evidence of some plaque disruption. In cases of failed wire crossings without angiographic dissections, the pathology was identical to chronic total occlusion model with dense fibrotic plaques, plaque neovascularization, some inflammatory cell infiltrate and frequent breaks in the internal elastic lamina with interceding fibrous tissue (FIGS. 4B and 5B). There was no evidence of wire injury in these cases. In cases of failed wire crossings due to angiographic dissections, these wire channels were evident outside the intimal plaque in the media and occasionally in the adventitial or peri-adventitial space. There were no detectable differences in the extent of vessel wall damage (such as disruption of internal elastic lamina or medial wall) between the collagenase treated and placebo treated arteries.

24 Hour Studies of Collagenase Effects in Chronic Total Occlusions

In order to determine that the collagenase formulation was in fact affecting the structure and extracellular matrix proteins in the occlusive arterial plaque, an additional 6 arteries (3 collagenase [450 μg], 3 placebo) were removed at 24 hours after the drug administration. No guide-wire attempts to cross these occlusions were made in order to assess the collagenase effects without the confounding effects of the guide wires. The arteries were also assessed for the presence of MMP-1 protein, collagen degradation products and gelatinase activity.

Interstitial Collagenase (MMP-1) Western Blot Analysis

Frozen arteries were pulverised in liquid nitrogen and extracted in ice cold extraction buffer (cocodylic acid 10 mM, NaCl 150 mM, $ZnCl_2$ 20 mM, $NaN_3$ 1.5 mM and SDS 1% w/v). For detection of collagen degradation products, extracts containing 50 μg protein were fractionated on 4-20% trisglycine gels under reducing conditions and electrotransferred onto nitrocellulose membranes (Bio-Rad). COL 2¾ C short polyclonal rabbit IgG (HDM Diagnostics & Imaging Inc, Toronto) was used as a primary antibody at a dilution of 1:1000 and anti rabbit IgG-HRP (Santa Cruz Biotechnology) was used as a secondary antibody. To detect interstitial collagenase (MMP-1) protein, extracts containing 50 μg of protein were separated under non-reducing conditions and electroblotted onto nitrocellulose membranes. Anti-MMP-1 monoclonal antibody (Calbiochem) was used as a primary antibody at a dilution of 1:100 and anti mouse IgG-HRP (Santa Cruz Biotechnology) was used as a secondary antibody. To reveal secondary antibody, chemiluminescence detection system (ECL Plus, Amersham) was used followed by autoradiography.

The interstitial collagenase (MMP-1) Western blot analyses in both collagenase and placebo-treated arteries showed the presence of a band at ≈93 kD, confirming the presence of interstitial collagenase (MMP-1) (FIG. 7). This band was markedly increased in the collagenase-treated arteries compared to the placebo-treated arteries, showing increased interstitial collagenase (MMP-1) protein in collagenase-treated arteries at 24 hours after treatment.

Gelatinase Zymography

Gelatin zymography was performed as previously described[52]. Gelatin zymography showed an increase of an 92-kD gelatinase (MMP-9) only in collagenase-treated arteries with no activity evident in placebo-treated arteries (FIG. 8). Lytic bands were present at 92 and 82 kD, reflecting both the proenzyme and the activated forms of MMP-9. Both collagenase and placebo-treated arteries had evidence of a 72-kD gelatinase (MMP-2).

Collagen Degradation Products

Degraded collagen was assessed by western blot analysis under reducing conditions with a polyclonal antibody directed against cleaved human type II collagen (col 2¾C, dilution 1/1000, Diagnostic Imaging). Collagen degradation products were identified in both placebo-treated and collagenase-treated arteries, with a marked increase in collagenase treated arteries (FIG. 9).

Pathology of Chronically Occluded Arteries Treated by Collagenase or Placebo

There was extensive degradation of the occlusive plaque evident in 2 of the 3 arteries treated with collagenase which was not present in any of the placebo treated arteries (FIG. 10). The placebo treated arteries had identical pathology to the arteries previously described in the chronic total occlusion model.

An experimental model to study chronic arterial occlusions and a composition and amount of collagenase containing formulation that can facilitate guidewire crossing have been discovered. A chronic arterial occlusion model was developed in the femoral arteries of rabbits by applying temporary occlusive ligatures supplemented with thrombin injections to promote acute thrombosis and then waiting an average of 16 weeks for the acute thrombotic occlusion to develop into a chronic fibrotic occlusion, analogous to chronic human arterial occlusions. The local delivery of 450 μg of a collagenase containing formulation through the wire-port of an over-the-wire angioplasty balloon over a 60 minute period while the balloon is inflated can cause collagen degradation, increased MMP-1 and MMP-9 activity and demonstrable lysis of plaque components within the occluded artery at 24 hours compared to placebo treated arteries. This local delivery of collagenase can increase the success rates of guidewire crossing at 72 hours but not at 1 hour after collagenase administration. Thus, a waiting period of 24-72 hours is required to allow the collagenase to degrade the plaque prior to attempting guidewire crossing. These effects of collagenase on the occlusive plaque can be achieved without damage to the outer layers of the vessel wall (media and adventitia) and without aneurysm formation.

REFERENCES

1. Baim D S, Ignatius E J. Use of coronary angioplasty: Results of a current survey. Am J Cardiol 1988; 61:3G-8G
2. Savage R, Holman J, Gruentzig A R, King S, Douglas J, Tankersley R. Can percutaneous transluminal coronary angioplasty be performed in patients with total occlusion? [abstract]. Circulation 1982; 66 Suppl II:II-330
3. Topol E J, Serruys P W. Frontiers in interventional cardiology. Circulation 1998; 98: 1802-1820
4. Detre K, Holubkove R, Kelsey S, Cowley M, Kent W, Williams D, Myler R, Faxon D et al. Percutaneous transluminal angioplasty in 1985-1986 and 1977-1981. The Heart, Lung, and Blood Institute Registry. N Engl J Med 1988; 318:265-270
5. Bell M R, Berger P B, Bresnahan J F, Reeder G S, Bailey K R, Holmes D R Jr. Initial and long-term outcome of 354 patients after coronary balloon angioplasty of total coronary artery occlusions. Circulation 1992; 85:1003-11
6. Safian R D, McCabe C H, Sipperly M E, McKay R G, Baim D S. Initial success and long-term follow-up of percutaneous transluminal coronary angioplasty in chronic total occlusions versus conventional stenoses. Am J Cardiol 1988; 61:23G-28G
7. Suero J A, Marso S P, Jones P G, Laster S B, Huber K C, Giorgi L V, Johnson W L, Rutherford B D. Procedural outcomes and long-term survival among patients undergoing percutaneous coronary intervention of a chronic total occlusion in native coronary arteries: a 20-year experience. J Am Coll Cardiol 2001; 38:409-14.
8. Sirnes P A, Golf S, Myreng Y, Molstad P, Emanuelsson H, Albertsson P, Brekke M, Mangschau A, Endresen K, Kjekshus J. Stenting in chronic coronary occlusion (SICCO): A randomized, controlled trial of adding stent implantation after successful angioplasty. J Am Coll Cardiol 1996; 28:1444-51
9. Buller C E, Dzavik V, Carere R G, Mancini G B, Barbeau G, Lazzam C, Anderson T J, Knudtson M L, Marquis J F, Suzuki T, Cohen E A, Fox R S, Teo K K. Primary stenting versus balloon angioplasty in occluded coronary arteries: the Total Occlusion Study of Canada (TOSCA). Circulation 1999; 100:236-242
10. Rubartelli P, Niccoli L, Verna E, Giachero C, Zimarino M, Fontanelli A, Vassanelli C, Campolo L, Martuscelli E, Tommasini G. Stent implantation versus balloon angioplasty in chronic coronary occlusions: results from the GISSOC trial. J Am Coll Cardiol 1998; 32:90-96.
11. Ellis S G, Shaw R E, Gershony G, et al. Risk factors, time course and treatment effect for restenosis after successful percutaneous transluminal coronary angioplasty of chronic total occlusion. Am J Cardiol 1989; 63:897-901.
12. Melchior J P, Meier B, Urban P, et al. Percutaneous transluminal coronary angioplasty for chronic total coronary arterial occlusion. Am J Cardiol 1988; 59:535-538.
13. Stone G W, Rutherford B D, McConahay D R, Johnson W L Jr, Giorgi L V, Ligon R W, Hartzler G O. Procedural outcome of angioplasty for total coronary artery occlusion: an analysis of 971 lesions in 905 patients. J Am Coll Cardiol 1990; 15:849-56.
14. Ivanhoe R J, Weintraub W S, Douglas J S Jr, et al. Percutaneous transluminal coronary angioplasty of chronic total occlusions. Primary success, restenosis, and long-term clinical follow-up. Circulation 1992; 85:106-15.
15. Haine E, Urban P, Dorsaz P A, Meier B. Outcome and complications of 500 consecutive chronic total occlusion coronary angioplasties [abstract]. J Am Coll Cardiol 1993; 21:138A.
16. Lefevre T. Louvard Y. Loubeyre. C. Dumas P. Piechaud J F. Krol M. Benslimane A. Premchand R K. Morice M C. A randomized study comparing two guidewire strategies for angioplasty of chronic total coronary occlusion. American Journal of Cardiology 2000; 85:1144-7.
17. Kahler J. Koster R. Brockhoff C. Reimers J. Baldus S. Terres W. Meinertz T. Hamm C W. Initial experience with a hydrophilic-coated guidewire for recanalization of chronic coronary occlusions. Cathet Cardiovasc Interven 2000; 49:45-50.
18. Maiello L, Colombo A, Giatuossi R, et al Coronary angioplasty of chronic occlusions: factors predictive of procedural success. Am Heart J 1992; 124:581-4
19. Puma J A, Sketch M H, Tcheng J E, et al. Percutaneous revascularization of chronic coronary occlusions—an overview. J Am Coll Cardiol 1995; 26:1-11
20. Tan W, Sulke A N, Taub N A, Watts E, Sowton E. Determinants of success of coronary angioplasty in patients with a chronic total occlusion: a multiple logistic regression model to improve selection of patients. Br Heart J 1993; 70:126-31
21. Serruys P W, Umans V, Heyndrickx G R, et al. Elective PTCA of totally occluded coronary arteries not associated with acute myocardial infarction: short term and long-term results. Eur Heart J 1985; 6:2-12
22. Jaup T, Allemann Y, Urban P, Dorsaz P A, Chatelain P, Brzostek T, Verine V, Rutishauser W, Meier B. The Magnum wire for percutaneous coronary balloon angioplasty in 723 patients. J Invas Cardiology 1995; 7:259-64.
23. Rees M R, Michalis L K. Activated-guidewire technique for treating chronic coronary artery occlusion. Lancet 1995; 346:943-4.
24. Rees M R, Michalis L K, Pappa E C, Loukas S, Goudevenos J A, Sideris D A. The use of soft and flexible guidewires in the treatment of chronic total coronary occlusions by activated guidewire angioplasty. Br J Radiol 1999; 72:162-7.
25. Hamburger J N, et al. Recanalization of chronic total coronary occlusions with a laser guide wire: a pilot study. J Am Coll Cardiol 1997; 30:649-656
26. Oesterle S N, Bittl J A, Leon M B, et al. Laser wire for crossing chronic total occlusions: A learning phase results from the U.S. TOTAL trial. Total Occlusion Trial with Angioplasty by Using a Laser Wire. Cathet Cardiovasc Diagn 1998; 44:235-243

27. Schofer J, Rau T, Schluter M, Mathey D G. Short-term results and intermediate-term follow-up of laser wire recanalization of chronic coronary artery occlusions: a single center experience. J Am Coll Cardiol 1997; 30:1722-1728
28. Jacksch R, Papadakis E, Rosanowski C, Toker Y. Comparison of three different techniques in reopening chronic coronary artery occlusion [abstract]. Circulation 1992; 86: Suppl I-I-781
29. Serruys P W, Hamburger J N, Koolen J J, Fajadet J, Haude M, Klues H, Seabra-Gomes R, Corcos T, Hamm C, Pizzuli L, Meier B, Mathey D, Fleck E, Taeymans Y, Melkert R. Teunissen Y. Simon R. Total occlusion trial with angioplasty by using laser guidewire. The TOTAL trial. Eur Heart J 2000; 21:1797-805.
30. Ruocco N A, Currier J W, Jacobs A K, Ryan T J, Faxon D P. Experience with low-dose intracoronary recombinant tissue-type plasminogen activator for nonacute total occlusions before percutaneous transluminal coronary angioplasty. Am J Cardiol 1991; 68:1609-13
31. Zidar F J, Kaplan B M, O'Neill W W, Jones D E, Schreiber T L, Safian R D, Ajluni S C, Sobolski J, Timmis G C, Grines C L. Prospective, randomized trial of prolonged intracoronary urokinase infusion for chronic total occlusions in native coronary arteries. J Am Coll Cardiol 1996; 27:1406-12.
32. Ruocco N A Jr, Ring M E, Holubkov R, Jacobs A K, Detre K K, Faxon D P. Results of coronary angioplasty of chronic total occlusions: the National Heart, Lung, and Blood Institute 1985-1986 Percutaneous Transluminal Angioplasty Registry. Am J Cardiol 1992; 69:69-76
33. Trappe H J, Lichtlen P R, Klein H, Wenzlaff P, Hartwig C A. Natural history of single vessel disease. Risk of sudden coronary death in relation to coronary anatomy and arrhythmia profile. Eur Heart J 1989; 10:514-524
34. Dzavik V, Beanlands D S, Davies R F, Leddy D, Marquis J-F, Teo K K, Ruddy T D, Burton J R, Humen D P. Effects of late percutaneous transluminal coronary angioplasty of an occluded infarct-related coronary artery on left ventricular function in patients with a recent (<6 weeks) Q-wave acute myocardial infarction (Total Occlusion post-Myocardial Infarction Intervention Study [TOMIIS]—A pilot study. Am J Cardiol 1994; 73:856-61
35. Pizzetti G, Belotti G, Margonato A, Cappelletti A, Chierchia S. Coronary recanalization by elective angioplasty prevents ventricular dilatation after anterior myocardial infarction. J Am Coll Cardiol 1996; 28:837-45
36. Sirnes P A. Myreng Y. Molstad P. Bonarjee V. Golf S. Improvement in left ventricular ejection fraction and wall motion after successful recanalization of chronic coronary occlusions. Eur Heart J 1998; 19:273-81.
37. Danchin N. Angioi M. Cador R. Tricoche O. Dibon O. Juilliere Y. Cuilliere M. Cherrier F. Effect of late percutaneous angioplastic recanalization of total coronary artery occlusion on left ventricular remodeling, ejection fraction, and regional wall motion. American Journal of Cardiology 1996; 78:729-35.
38. Engelstein E. Terres W. Hofmann D. Hansen L. Hamm C W. Improved global and regional left ventricular function after angioplasty for chronic coronary occlusion. Clin Invest 1994; 72:442-7.
39. Srivatsa S S, Edwards W D, Boos C M, Grill D E, Sangiorgi G M, Garratt K N, Schwartz R S, Holmes D R Jr. Histologic correlates of angiographic chronic total coronary artery occlusions: influence of occlusion duration on neovascular channel patterns and intimal plaque composition. J Am Coll Cardiol 1997; 29:955-63

40. Meier B. Chronic Total Occlusion. In: Textbook of Interventional Cardiology. Editior: E. Topol. W.B. Saunders, Philadelphia 1994:318-338
41. Bartos F, Ledvina M. Collagen, elastin, and desmosines in three layers of bovine aortae of different ages. Exp Gerontol 1979; 14:21-26
42. Hosoda Y, Kawano K, Yamasawa F, Ishii T, Shibata T, Inayama S. Age dependent changes of collagen and elastin content in human aorta and pulmonary artery. Angiology 1984; 35:615-21
43. Mayne R. Collagenous proteins of blood vessels. Arteriosclerosis 1986; 6:585-593
44. Katsuda S, Okada Y, Minamoto T, Oda Y, Matsui Y, Nakanishi I. Collagens in human atherosclerosis: immunohistochemical analysis using collagen type-specific antibodies. Arterioscler Thromb 1992; 12:494-502
45. Woessner J F Jr. Matrix metalloproteinases and their inhibitors in connective tissue remodelling. FASEB J 1991; 5:2145-2154
46. Matrisian L M. The matrix-degrading metalloproteinases. Bioessays 1992; 14:455-463
47. Dollery C M, McEwan J R, Henney A M. Matrix metalloproteinases and cardiovascular disease. Circ Res 1995; 77:863-868
48. Rosenberg G A, Mun-Bryce S, Wesley M, Kornfeld M. Collagenase-induced intracerebral hemorrhage in rats. Stroke 1990; 21:801-807
49. Rosenberg G A, Estrada E Y. Atrial natriuretic peptide blocks hemorrhagic brain edema after 4-hour delay in rats. Stroke 1995; 26:874-877
50. Del Bigio M R, Yan H-J, Buist R, Peeling J. Experimental intracerebral hemorrhage in rats: magnetic resonance imaging and histopathological correlates. Stroke 1996; 27:2312-2318
51. Kerényi T, Merkel V, Szabolcs Z, Pusctai P, Nadasy G. Local enzymatic treatment of atherosclerotic plaques. Experimental and Molecular Pathology 1988; 49:330-338
52. Strauss B H, Robinson R, Batchelor W B, Chisholm R J, Ravi G, Natarajan M K, Logan R A, Mehta S R, Levy D E, Ezrin A M, Keeley. In vivo collagen turnover following experimental balloon angioplasty injury and the role of matrix metalloproteinases. Circ Res 1996; 79:541-550
53. Hohnloser S H, P Franck P, Klingenheben T, Zabel M, Just H. Open infarct artery, late potentials, and other prognostic factors in patients after acute myocardial infarction in the thrombolytic era. A prospective trial. Circulation 1994; 90:1747-56
54. Hermosillo A G, Dorado M, Casanova J M, Ponce de Leon S, Cossio J, Kersenovich S, Colin L, Iturralde P. Influence of infarct-related artery patency on the indexes of parasympathetic activity and prevelance of late potentials in survivors of acute myocardial infarction. J Am Coll Cardiol 1993; 22:695-706
55. Huikuri H V, Koistinen M J, Airaksinen K E, Ikaheimo M J. Significance of perfusion of the infarct related coronary artery for susceptibility to ventricular tachyarrhythmias in patients with previous myocardial infarction. Heart 1996; 76:91-92.

The invention claimed is:

1. A method of treating a fibrotic chronic total occlusion associated with atherosclerotic disease of an artery of an animal, which occlusion cannot be crossed by a guide wire, the method comprising the steps of:
   a) administering a therapeutically effective amount of a collagenase enzyme containing formulation having an amount of the collagenase that softens the occlusion without damaging the arterial wall adjacent the occlusion, and retaining the formulation adjacent the occlusion for a collagenase enzyme treatment period of at least 10 minutes;
   b) waiting for a pre-angioplasty waiting period to degrade the occlusion sufficiently so as to soften the occlusion to permit crossing thereof by a guide wire; and
   c) crossing the occlusion with an angioplasty guide wire.

2. The method of claim 1 wherein the collagenase enzyme treatment period is between about 20 minutes and about 100 minutes.

3. The method of claim 2 wherein the collagenase enzyme treatment period is between about 50 minutes and about 80 minutes.

4. The method of claim 3 wherein the collagenase enzyme treatment period is about 60 minutes.

5. The method claim 1 wherein the formulation comprises 50-2000 µg of collagenase.

6. The method claim 5 wherein the formulation comprises a dosage of from about 150 µg to 500 µg of collagenase.

7. The method of claim 1 wherein the duration of the pre-angioplasty waiting period is between about 1 hour and about 108 hours.

8. The method of claim 7 wherein the duration of the pre-angioplasty waiting period is between about 24 hours and about 72 hours.

9. The method of claim 1 wherein the duration of the pre-angioplasty waiting period is about 24 hours.

10. The method of claim 1 wherein the formulation is infused into the artery lumen adjacent to the occlusion.

11. The method of claim 10 wherein the infusion of the collagenase enzyme containing formulation is through the wire port of an angioplasty catheter.

12. The method of claim 10 wherein the infusion of the collagenase enzyme containing formulation is through an infusion needle.

13. The method of claim 10 wherein the infusion of the collagenase enzyme containing formulation is through a catheter.

14. The method of claim 1, wherein the collagenase is type 1A collagenase.

15. The method of claim 5, wherein the collagenase is type 1A collagenase.

16. The method of claim 7, wherein the collagenase is type 1A collagenase.

17. The method of claim 1, wherein the occlusion is at least about 10 weeks old.

18. The method of claim 17, wherein the occlusion is at least 12 weeks old.

19. The method of claim 18, wherein the occlusion is at least about 16 weeks old.

20. The method claim 17 wherein the formulation comprises 50-2000 µg of collagenase.

21. The method claim 18 wherein the formulation comprises 50-2000 µg of collagenase.

22. The method claim 19 wherein the formulation comprises 50-2000 µp of collagenase.

23. The method of claim 17 wherein the duration of the pre-angioplasty waiting period is between about 1 hour and about 108 hours.

24. The method of claim 23 wherein the duration of the pre-angioplasty waiting period is between about 12 hours and about 86 hours.

25. The method of claim 24 wherein the duration of the pre-angioplasty waiting period is between about 24 hours and about 72 hours.

26. The method of claim 5 wherein the duration of the pre-angioplasty waiting period is between about 1 hour and about 108 hours.

27. The method of claim 26 wherein the duration of the pre-angioplasty waiting period is between about 12 hours and about 86 hours.

28. The method of claim 27 wherein the duration of the pre-angioplasty waiting period is between about 24 hours and about 72 hours.

29. The method of claim 17 wherein the collagenase enzyme treatment period is between about 20 minutes and about 100 minutes.

30. The method of claim 29 wherein the collagenase enzyme treatment period is between about 50 minutes and about 80 minutes.

31. The method of claim 17, wherein the collagenase is type 1A collagenase.

32. A method of treating a fibrotic chronic total occlusion associated with atherosclerotic disease of an artery of an animal, which occlusion cannot be crossed by a guide wire, the method comprising the steps of:
   a) advancing an angioplasty balloon catheter on a guide wire into the artery;
   b) inflating the balloon;
   c) administering a therapeutically effective amount of a collagenase enzyme containing formulation having an amount of the collagenase that softens the occlusion without damaging the arterial wall into the space between the balloon and the occlusion so as to be adjacent the occlusion;
   b) removing the balloon after a collagenase enzyme treatment period of at least 10 minutes;
   e) waiting for a pre-angioplasty waiting period to degrade the occlusion sufficiently so as to soften the occlusion to permit crossing thereof by a guide wire; and
   f) crossing the occlusion with an angioplasty guide wire.

33. The method of claim 32 wherein the duration of the pre-angioplasty waiting period is between about 1 hour and about 108 hours.

34. The method of claim 33 wherein the duration of the pre-angioplasty waiting period is between about 12 hours and about 86 hours.

35. The method of claim 34 wherein the duration of the pre-angioplasty waiting period is between about 24 hours and about 72 hours.

36. The method of claim 35 wherein the duration of the pre-angioplasty waiting period is about 24 hours.

37. The method of claim 33 wherein the formulation is infused into the artery lumen adjacent to the occlusion.

38. The method of claim 33 wherein the infusion of the formulation is through the wire port of an angioplasty catheter.

39. The method of claim 33 wherein the infusion of the formulation is through an infusion needle.

40. The method of claim 33 wherein the infusion of the formulation is through a catheter.

41. The method of claim 33 wherein the balloon is inflated to a pressure in the range of about 1-5 atmospheres.

42. The method of claim 33 wherein the balloon is inflated to a pressure of about 4 atmospheres.

43. The method of claim 32, wherein the formulation is infused under a pressure of between about 1 and 5 atmospheres.

44. The method of claim 38 wherein the formulation is infused under a pressure in the range of about 0.5 atmospheres to 3.5 atmospheres.

45. The method of claim 44 wherein the formulation is infused under a pressure in the range of about 1 to 2 atmospheres.

46. The method of claim 32 wherein the balloon is inflated to a pressure in the range of about 1-5 atmospheres.

47. The method of claim 32 wherein the formulation is infused under a pressure in the range of about 0.5 atmospheres to 3.5 atmospheres.

48. The method of claim 47 wherein the formulation is infused under a pressure in the range of about 1 to 2 atmospheres.

49. The method claim 32 wherein the formulation comprises 50-2000 µg of collagenase.

50. The method claim 49 wherein the formulation comprises a dosage of from about 150 µg to 500 µg of collagenase.

51. The method of claim 32, wherein the collagenase is type 1A collagenase.

52. The method of claim 33, wherein the collagenase is type 1A collagenase.

53. The method of claim 49, wherein the collagenase is type 1A collagenase.

54. The method of claim 32, wherein the occlusion is at least about 10 weeks old.

55. The method of claim 54, wherein the occlusion is at least 12 weeks old.

56. The method of claim 55, wherein the occlusion is at least about 16 weeks old.

57. The method claim 54 wherein the formulation comprises 50-2000 µg of collagenase.

58. The method claim 55 wherein the formulation comprises 50-2000 µg of collagenase.

59. The method claim 56 wherein the formulation comprises 50-2000 µp of collagenase.

60. The method of claim 54 wherein the duration of the pre-angioplasty waiting period is between about 1 hour and about 108 hours.

61. The method of claim 60 wherein the duration of the pre-angioplasty waiting period is between about 12 hours and about 86 hours.

62. The method of claim 61 wherein the duration of the pre-angioplasty waiting period is between about 24 hours and about 72 hours.

63. The method of claim 49 wherein the duration of the pre-angioplasty waiting period is between about 1 hour and about 108 hours.

64. The method of claim 63 wherein the duration of the pre-angioplasty waiting period is between about 12 hours and about 86 hours.

65. The method of claim 64 wherein the duration of the pre-angioplasty waiting period is between about 24 hours and about 72 hours.

66. The method of claim 32 wherein the collagenase enzyme treatment period is between about 20 minutes and about 100 minutes.

67. The method of claim 66 wherein the collagenase enzyme treatment period is between about 50 minutes and about 80 minutes.

68. The method of claim 54 wherein the collagenase enzyme treatment period is between about 20 minutes and about 100 minutes.

69. The method of claim 68 wherein the collagenase enzyme treatment period is between about 50 minutes and about 80 minutes.

70. The method of claim 54, wherein the collagenase is type 1A collagenase.

71. The method of claim 55, wherein the collagenase is type 1A collagenase.

72. A method of treating a fibrotic chronic total occlusion associated with atherosclerotic disease of an artery of an animal, and which occlusion cannot be crossed by a guide wire, the method comprising the steps of:
- a) administering a therapeutically effective amount of a collagenase enzyme containing formulation having an amount of the collagenase that softens the occlusion without damaging the arterial wall to be in direct contact with the occlusion;
- b) retaining the formulation adjacent the occlusion for a collagenase enzyme treatment period of at least about 10 minutes;
- c) waiting for a pre-angioplasty waiting period to degrade the occlusion sufficiently so as to soften the occlusion to permit crossing thereof by a guide wire; and
- b) crossing the occlusion with an angioplasty guide wire.

73. The method of claim 72, wherein the collagenase is type 1A collagenase.

74. The method of claim 72, wherein the occlusion is at least about 10 weeks old.

75. The method of claim 74, wherein the occlusion is at least 12 weeks old.

76. The method of claim 75, wherein the occlusion is at least about 16 weeks old.

77. The method claim 72 wherein the formulation comprises 50-2000 μg of collagenase.

78. The method claim 74 wherein the formulation comprises 50-2000 μg of collagenase.

79. The method claim 75 wherein the formulation comprises 50-2000 μg of collagenase.

80. The method claim 76 wherein the formulation comprises 50-2000 μp of collagenase.

81. The method of claim 72 wherein the duration of the pre-angioplasty waiting period is between about 1 hour and about 108 hours.

82. The method of claim 81 wherein the duration of the pre-angioplasty waiting period is between about 12 hours and about 86 hours.

83. The method of claim 82 wherein the duration of the pre-angioplasty waiting period is between about 24 hours and about 72 hours.

84. The method of claim 74 wherein the duration of the pre-angioplasty waiting period is between about 1 hour and about 108 hours.

85. The method of claim 84 wherein the duration of the pre-angioplasty waiting period is between about 12 hours and about 86 hours.

86. The method of claim 85 wherein the duration of the pre-angioplasty waiting period is between about 24 hours and about 72 hours.

87. The method of claim 77 wherein the duration of the pre-angioplasty waiting period is between about 1 hour and about 108 hours.

88. The method of claim 87 wherein the duration of the pre-angioplasty waiting period is between about 12 hours and about 86 hours.

89. The method of claim 88 wherein the duration of the pre-angioplasty waiting period is between about 24 hours and about 72 hours.

90. The method of claim 72 wherein the collagenase enzyme treatment period is between about 20 minutes and about 100 minutes.

91. The method of claim 90 wherein the collagenase enzyme treatment period is between about 50 minutes and about 80 minutes.

92. The method of claim 74 wherein the collagenase enzyme treatment period is between about 20 minutes and about 100 minutes.

93. The method of claim 92 wherein the collagenase enzyme treatment period is between about 50 minutes and about 80 minutes.

94. The method of claim 81, wherein the collagenase is type 1 A collagenase.

95. The method of claim 77, wherein the collagenase is type 1A collagenase.

* * * * *